(12) United States Patent
Noda et al.

(10) Patent No.: US 7,910,142 B2
(45) Date of Patent: Mar. 22, 2011

(54) METHOD OF PRODUCING SEAWEED PASTE AND SEAWEED PASTE OBTAINED BY SUCH A METHOD

(75) Inventors: Fumio Noda, Nanao (JP); Minoru Noda, Nanao (JP); Tetsuya Nakamura, Nanao (JP); Isamu Yoshino, Nanao (JP); Kiyoharu Miyamoto, Nanao (JP); Kazuya Yamada, Ashikaga (JP); Masayuki Wakabayashi, Nanao (JP); Tomohiro Shibahara, Nanao (JP)

(73) Assignee: Sugiyo Co., Ltd., Nanao-shi (JP)

( * ) Notice: Subject to any disclaimer, the term of this patent is extended or adjusted under 35 U.S.C. 154(b) by 151 days.

(21) Appl. No.: 12/177,281

(22) Filed: Jul. 22, 2008

(65) Prior Publication Data

US 2009/0028899 A1    Jan. 29, 2009

(30) Foreign Application Priority Data

Jul. 24, 2007    (JP) .................. 2007-191973

(51) Int. Cl.
*A61K 36/00*    (2006.01)
*A61K 36/02*    (2006.01)
*A23L 1/05*    (2006.01)

(52) U.S. Cl. .................... 424/725; 424/195.17; 426/575

(58) Field of Classification Search .......... None
See application file for complete search history.

(56) References Cited

U.S. PATENT DOCUMENTS 5,843,762 A * 12/1998 Moll .......................... 435/257.1
6,338,856 B1 * 1/2002 Allen et al. .................... 424/442

FOREIGN PATENT DOCUMENTS

JP    10-155462    6/1998
JP    10155462 A *    6/1998
KR    2004074030 A *    8/2004

OTHER PUBLICATIONS

Murano et al, Investigation of the carrageenans extracted from *Solieria filiformis* and *Agrdhiella subulata* from Mar Piccolo, Taranto,Marine Chemistry 58 (1997) 319-325.*

* cited by examiner

*Primary Examiner* — Qiuwen Mi
(74) *Attorney, Agent, or Firm* — Renner, Otto, Boisselle & Sklar, LLP

(57) ABSTRACT

A method of producing seaweed paste including the steps of: placing seaweed, a chelating agent and water in a tank; and stirring the resulting composition at 0-20° C. to cut the seaweed, wherein the interior of the tank is in a vacuum state. A method of producing seaweed paste having good texture, smell and flavor and seaweed paste obtained by such a method are provided. A method of producing seaweed paste having good quality, which does not require treatment at a high temperature and thus can give a color and smell inherent to seaweeds and seaweed paste obtained by such a method are provided. A method of producing seaweed paste which requires a short treatment time, has good productivity and can reduce production costs, and seaweed paste obtained by such a method are provided.

8 Claims, 2 Drawing Sheets

METHOD OF PRODUCING SEAWEED PASTE AND SEAWEED PASTE OBTAINED BY SUCH A METHOD

BACKGROUND OF THE INVENTION

1. Field of the Invention

The present invention relates to a method of producing seaweed paste of *Undaria pinnatifida,* sea tangles, *Nemacystus decipiens* and the like, and seaweed paste obtained by such a method.

2. Description of the Related Art

It is said that the amount of production of seaweeds in the world is 20,000,000 t/year, and that 750,000 t/year of seaweeds are used in Japan. However, it is said that a much greater amount of seaweeds are not effectively used and disposed as industrial wastes.

In U.S.A., it is believed that seaweeds are effective as substitutes for starch and fats, and studies on seaweeds have been actively carried out. In Japan, people have started to recognize seaweeds as good materials for health. In particular, sticky components in seaweeds are noted in all foods, and thus they reached to find various functions of seaweeds, for example, (1) action of improving bowel movement, (2) anticoagulant action, (3) anticancer action, (4) action of reducing cholesterol, (5) action of decreasing blood pressure, (6) antiviral action, (7) antiallergic action and (8) therapeutic effect on indefinite complaint.

However, seaweeds are not utilized extensively for their low processing suitability.

Conventionally, paste of seaweeds refined to a unit such that the seaweeds can be entirely absorbed in the body has been developed. However, seaweed particles in such a paste are rough and uneven, and such a paste does not have sufficient processing suitability.

Japanese Laid-Open Patent Publication No. 10-155462 (Patent Document 1) discloses the following method of producing noodle-shaped solidified food of *Undaria pinnatifida.*

Dried *Undaria pinnatifida* which has swelled by addition of water is placed and ground in a vacuum-heating/cooling kettle with a high-speed cutter. After adjusting the pH level to pH 5-6 with an acidulant, 0.8-1% by weight of cellulase is added to the *Undaria pinnatifida,* and the mixture is heated and stirred for 30 minutes to 1 hour at 40-50° C. 0.4-0.6% by weight sodium citrate is added and the mixture is heated and stirred for 1-2 hours at 70-80° C. A vacuum pump is simultaneously run, and the interior of the kettle is vacuumed to 0.5 atmosphere or less and is de-aerated. Finally, a cooling machine is run to cool the solution of *Undaria pinnatifida* to a normal temperature.

The resulting solution is discharged into 3-5% calcium lactate aqueous solution, thereby obtaining a noodle-shaped solidified food of *Undaria pinnatifida.*

However, as the production method as described above requires heat treatment of *Undaria pinnatifida* for 1-2 hours at 70-80° C., the *Undaria pinnatifida* experiences significant discoloration and loss of aromatic component, thereby deteriorating quality of the resulting food. Furthermore, relatively long time of treatment results in low productivity and high production costs of the solidified food.

[Patent Document 1] Japanese Laid-Open Patent Publication No. 10-155462

SUMMARY OF THE INVENTION

A method of producing seaweed paste and seaweed paste obtained by such a method of the present invention solve each of the above problems. The method of present invention includes the steps of: placing seaweed, chelating agent and water in a tank; and stirring the resulting composition at 0-20° C. to cut the seaweed, wherein the interior of the tank is in a vacuum state.

In a preferred embodiment, the chelating agent is blended at 0.5-5% by weight with respect to the total amount.

In a preferred embodiment, the chelating agent is at least one selected from the group consisting of citric acid, phosphoric acid, gluconic acid, phytic acid, salts thereof, methionine, cystein, EDTA, biodegradable chelating agent and HIDS.

In a preferred embodiment, a degree of vacuum of the tank is in the atmosphere of 50 mmHg to 700 mmHg.

In a preferred embodiment, the time for cutting treatment of the seaweed is 5-30 minutes.

In a preferred embodiment, an average particle size of the seaweed in the seaweed paste after cutting the seaweed is 5-100 µm.

Seaweed paste of the present invention is obtained by the above method, and the average particle size of the seaweed in the seaweed paste after cutting the seaweed is 5-100 µm.

Food, formulation, Japanese paper, film and concrete of the present invention contains the above seaweed paste.

Thus, the present invention can achieve the following purposes:

(1) providing a method of producing seaweed paste having good texture, smell and flavor and seaweed paste obtained by such a method;

(2) providing a method of producing seaweed paste having good quality, which does not require treatment at a high temperature and thus can give a color and smell inherent to seaweeds and seaweed paste obtained by such a method;

(3) providing a method of producing seaweed paste which requires a short treatment time, has good productivity and can reduce production costs, and seaweed paste obtained by such a method, and (4) providing foods, cosmetics, formulations, papers such as Japanese papers, and materials for building such as concrete, containing seaweed paste with small particle size.

The present inventors have made wholehearted study for developing seaweed paste having more smoothness and higher processing suitability. As a result, they found that seaweed paste which maintains color and flavor inherent to seaweeds, having small and even particle size and high processing suitability, can be obtained by cutting seaweed in the presence of a substance having chelating action, at 0-20° C. and under reduced pressure. It was found that such seaweed paste according to the present invention can be effectively used not only for foods but also for cosmetics, materials for building, and chemical products.

A method of producing seaweed paste according to the present invention includes the steps of: placing seaweed, chelating agent and water in a tank; and stirring the resulting composition at 0-20° C. in a vacuum state to cut the seaweed, seaweed paste can be obtained in which an average particle size of seaweed in the seaweed paste is 5-100 µm. Furthermore, as seaweed paste can be obtained at a low temperature of 0-20° C. and in a short time (for example, 5-30 minutes), smell, flavor and color unique to seaweeds are not lost. Thus, by treating seaweeds at a low temperature zone, deterioration and denaturation of seaweeds are prevented.

Furthermore, as seaweed paste having small seaweed particle can be obtained in a short treatment time and by a simple method, production costs are low, and working efficiency is high. Moreover, seaweed paste can be adjusted to have any viscosity, and thus quality thereof is stabilized.

If the obtained seaweed paste is added to a food, a food having smell and flavor of seaweed, good feeling on the tongue and smoothness can be obtained.

If the obtained seaweed paste is added to cosmetics, cosmetics having smell of seaweed, smoothness and good texture can be obtained.

If the obtained seaweed paste is added to a formulation, a formulation having small of seaweed and smoothness can be obtained.

If the obtained seaweed paste is added to Japanese paper or a material for building, a material for building having safety and good strength can be obtained.

EXAMPLES

Figure 1:
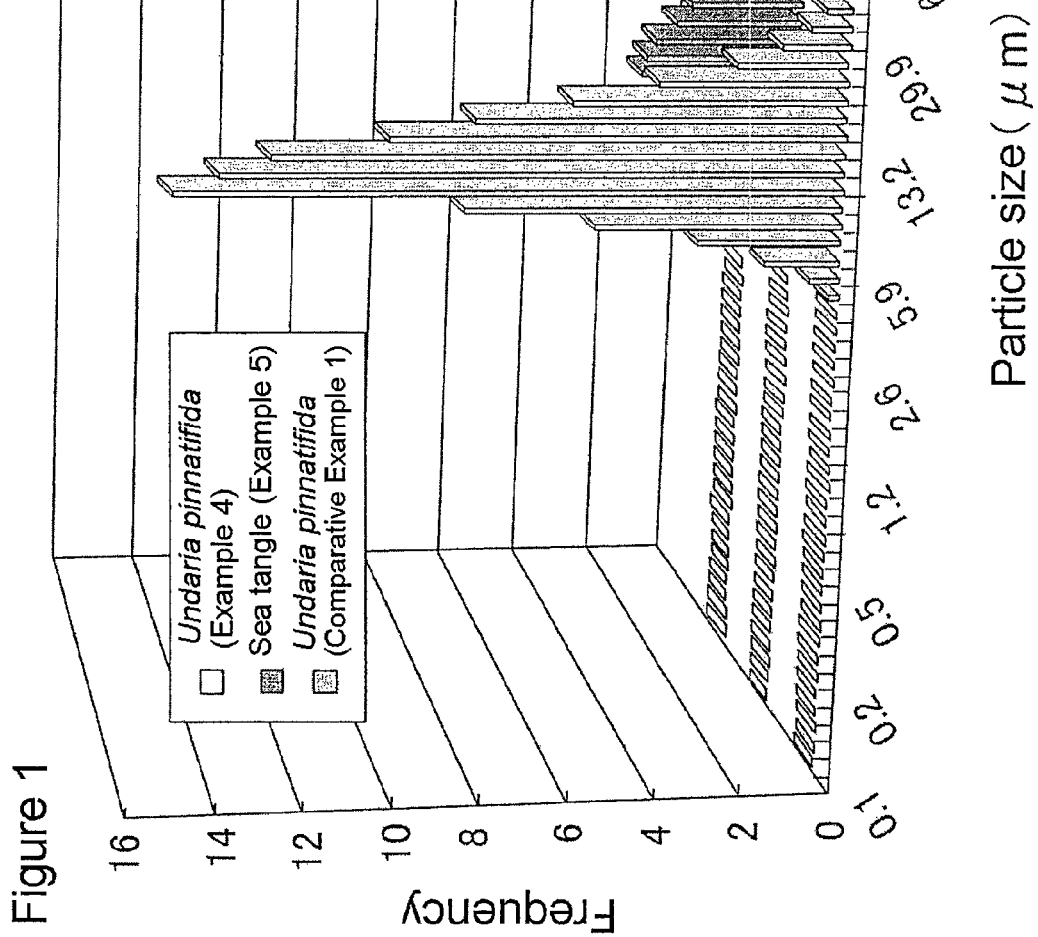
FIG. 1 is a diagram illustrating particle size distribution of seaweed paste.

Hereinafter, the present invention will be described in detail.

Regarding the seaweeds used in the present invention, *Undaria pinnatifida, Nemacystus decipiens,* sea tangles, *Eisenia bicyclis* and the like can be used. *Undaria pinnatifida, Nemacystus decipiens* and sea tangles are preferably used. For such seaweeds, it is possible to wash them in water and use them as raw seaweeds, and it is also possible to use salted and dried seaweeds after washing and soaking in water.

Chelating agents used in the present invention include citric acid, phosphoric acid, gluconic acid, phytic acid, salts thereof, methionine, cystein, EDTA (NTA, DTPA, GLDA, HEDTA, GEDTA, TTHA, HIDA, DHEG) biodegradable chelating agents, HIDS (Tetrasodium 3-Hydroxy-2,2'-Iminodisuccinate) and the like.

These chelating agents can be used alone or in combination of two or more.

Mixing ratio of seaweeds, water and a chelating agent placed in a tank is preferably such that water is 0-50 parts by weight and a chelating agent is 0.1-2.0 parts by weight with respect to 10 parts by weight of seaweed washed and soaked in water (water content: 70-90%). Particularly preferably, water is 5-25 parts by weight and the chelating agent is 0.3-1.0 parts by weight with respect to 10 parts by weight of seaweed.

An amount of the chelating agent added with respect to a total amount of a composition containing seaweed, water and a chelating agent is 0.5-5% by weight and more preferably, 1.0-4% by weight.

If an amount of the chelating agent added is less than 0.5% by weight with respect to the total amount of the composition, it is difficult to obtain seaweed paste with small particle size, and if the amount of the chelating agent added exceeds 5% by weight, flavor of the resulting seaweed paste is deteriorated.

If the amount of the chelating agent added is 1.0% or more, particularly 1.2% or more by weight, paste containing seaweed having small and even particle size can be obtained without requiring the use of an enzyme as described in Patent Document 1.

Furthermore, if water is used in a large amount with respect to the amount of seaweed, the use of such seaweed paste is limited, and thus an amount of water added is appropriately 0.5-3.0 parts by weight with respect to 1 part by weight of seaweed washed and soaked in water (water content: 70-90%).

Seaweed, water and a chelating agent in the blending amounts predetermined above are placed in a tank, and the composition in the tank is stirred and mixed at a temperature of 0-20° C. to cut the seaweed, wherein the interior of the tank is in a vacuum state.

Here, if cutting temperature (stirring temperature) is lower than 0° C., the resulting seaweed paste has a large particle size, and a long time is required until seaweed paste having a particle size below the predetermined particle size is obtained. If the cutting temperature is higher than 20° C., the smell, flavor and color unique to seaweeds are lost. Thus, a more preferable treatment temperature is 5-15° C.

The degree of vacuum of the interior of the tank at the stirring treatment may be under atmosphere of 50 mmHg-700 mmHg, and more preferably, the degree of vacuum is under atmosphere of 200 mmHg-600 mmHg. If the degree of vacuum at the stirring treatment is 700 mmHg or greater (under atmosphere close to atmospheric pressure), it is impossible to obtain paste containing seaweed with small particle size and even particle size distribution. To the contrary, if the degree of vacuum at the stirring treatment is 50 mmHg or less, the smell of seaweed tends to be lost, and costs of equipment including tank and the like are high.

In order to prevent deterioration and denaturation of seaweed, time for cutting treatment of seaweed is preferably short. For example, the time may be 5-30 minutes. Particularly, 7-25 minutes are particularly preferred. In stirring the interior of the tank, it is preferred to cut by rotating a rotative blade or the like initially at a low speed (1200-1500 rpm) and subsequently at a higher speed (2800-3000 rpm) for 2-3 minutes. It is preferred to perform such a stirring step for two or more times.

Regarding the tank, any known tank having a decompression apparatus such as a pump, stirring apparatus and a temperature controlling apparatus may be used. For the cutting treatment (cutting treatment), any instrument may be used as long as such an instrument can be controlled to be under reduced pressure at the time of the treatment. For example, a ball cutter, food cutter and the like can be preferably used.

Thus, a seaweed paste of the present invention is obtained. A particle size (arithmetic average) of seaweed in the obtained seaweed paste is preferably 5-300 μm, particularly preferably 10-100 μm, and the most preferably 10-60 μm.

When the seaweed is *Undaria pinnatifida,* a particle size (mode diameter), particle size (median diameter) and a particle size (arithmetic average) are preferably 6-20 μm, 6-20 μm and 8-20 μm, respectively. The most preferably, the particle size (mode diameter) is 6-10 μm, the particle size (median diameter) is 8-12 μm and the particle size (arithmetic average) is 10-16 μm.

When the seaweed is sea tangle, a particle size (mode diameter), particle size (median diameter) and a particle size (arithmetic average) are preferably 60-120 μm, 40-80 μm and 40-100 μm, respectively. The most preferably, the particle size (mode diameter) is 70-90 μm, the particle size (median diameter) is 50-70 μm and the particle size (arithmetic average) is 50-80 μm.

When the seaweed is Undaria pinnatifida, particle size distribution of the obtained seaweed paste is preferably a distribution having 80% or more particles with particle size of 5-20 μm with respect to all particles. When seaweed is sea tangle, a distribution having 80% or more particles with particle size of 10-150 μm with respect to all particles is preferred.

If an average particle size of seaweed in seaweed paste is more than 300 μm, processing stability is insufficient, and thus feeling on the tongue, texture, physical properties such as strength are impaired in a case of producing various products, cosmetics, formulations, sheets, films, materials for buildings and the like using such seaweed paste.

Seaweed paste of the present invention can be used by adding to various foods, cosmetics, formulations, daily necessities, materials for building and the like. An amount of the seaweed paste added may be usually 1-40% by weight, and preferably 5-20%. by weight. The amount added can be appropriately changed depending on various uses.

Foods include, for example, confectionery such as Japanese confectionery, Western-style confectionery, jelly and the like, bread, sweet bean paste, noodles (udon, Chinese noodle, Japanese buckwheat noodles, fried noodles and pasta), minced fish meat with seaweeds, seasonings such as jam, dressing, sauce and the like, gratin, stew, soup, spaghetti, hamburger, pizza, croquette, rice dish, fried rice, risotto, Japanese pot-au-feu, simmered dishes, stir-fried dishes, deep-fried dishes and the like.

Cosmetics include basic cosmetics (face toilet, milky lotion, cream, ointment, lotion, oil and pack), facial wash, skin wash, hair cosmetics such as shampoo, rinse and the like, and makeup cosmetics such as lipstick, foundation, blush, eye shadow, mascara and the like. The seaweed paste of the present invention can also be applied to bath salts, tooth paste, deodorizer, sanitary cottons, wet tissue and the like.

The seaweed paste can also be used for Japanese paper, films, sheets, materials for building such as concrete, medical formulation for external use, and the like.

When the seaweed paste of the present invention is used for foods, flavor and slimy feeling of seaweed can be provided, and advantages such as good feeling on the tongue and increased chewiness are also achieved. When the seaweed paste is added to daily necessities and materials for building, an advantage is that physical properties increase without losing safety.

Examples

Hereinafter, the present invention will be specifically explained by way of Examples, but is not limited to the present Examples. In the Examples shown below, all "%" means "% by weight".

Example 1

Effect of the Degree of Vacuum 10 kg of *Undaria pinnatifida* (water content: 90%) soaked with water after washing under flowing water was placed in a tank. 0.5 kg of sodium citrate and 5 kg of water were added, and the compositions of these components were respectively subjected to a cutting treatment (treatment using a cutter) using a Stephen cutter for 5 minutes at 10° C. under the vacuum conditions of the tank as shown for the classes tested in Table 1.

Particle size of the resulting *Undaria pinnatifida* paste was measured using a granulometer LA-920 produced by Horiba Ltd. Under atmosphere where a degree of vacuum in the tank was 600 mmHg or less, the average particle size was 20 μm or less, and a highly homogeneous *Undaria pinnatifida* paste could be obtained. The results are shown in Table 1.

TABLE 1

| Class | Degree of vacuum (mmHg) | Average particle size (μm) |
| --- | --- | --- |
| Control | 760 | 250 |
| Test-1 | 700 | 150 |

TABLE 1-continued

| Class | Degree of vacuum (mmHg) | Average particle size (μm) |
| --- | --- | --- |
| Test-2 | 600 | 20 |
| Test-3 | 500 | 15 |
| Test-4 | 400 | 11 |
| Test-5 | 300 | 10 |
| Test-6 | 200 | 10 |
| Test-7 | 100 | 10 |
| Test-8 | 50 | 10 |

Example 2

Effect of the Amount of a Chelating Agent Added 10 kg of *Undaria pinnatifida* (water content: 90%) soaked with water after washing under flowing water was placed in a tank. Sodium citrate was added in amounts shown for classes to be tested in Table 2 with respect to the total amount, and 5 kg of water was further added. The compositions of these components were respectively subjected to a cutting treatment (treatment using a cutter) using a Stephen cutter for 5 minutes at 10° C. under the atmosphere where the degree of vacuum in the tank is 400 mmHg.

Particle size of the resulting *Undaria pinnatifida* paste was measured. At 0.5% or more sodium citrate addition, the particle size was significantly low, and a highly homogeneous *Undaria pinnatifida* paste could be obtained.

When the amount of sodium citrate added was more than 5%, flavor inherent to *Undaria pinnatifida* was lost.

Thus, it was judged that an appropriate amount of the chelating agent that should be added was 0.5-5.0%. The results are shown in Table 2.

TABLE 2

| Class | Added amount (%) | Particle size (μm) |
| --- | --- | --- |
| Control | 0 | 300 |
| Test-1 | 0.1 | 120 |
| Test-2 | 0.5 | 20 |
| Test-3 | 1.0 | 10 |
| Test-4 | 2.0 | 10 |
| Test-5 | 3.0 | 10 |
| Test-6 | 4.0 | 10 |
| Test-7 | 5.0 | 9 |
| Test-8 | 6.0 | 9 |
| Test-9 | 7.0 | 9 |

Example 3

Effect of the Type of the Chelating Agent 10 kg of *Undaria pinnatifida* (water content: 90%) soaked with water after washing under flowing water was placed in a tank. 0.2 kg of the chelating agent shown for the classes to be tested in Table 3 was added, and 5 kg of water was further added. The compositions of these components were respectively subjected to a cutting treatment (treatment using a cutter) using a Stephen cutter for 5 minutes at 10° C. under the atmosphere where the degree of vacuum in the tank is 400 mmHg.

Particle size of the resulting *Undaria pinnatifida* paste was measured. Addition of any class of chelating agent resulted in small particle size, and smooth *Undaria pinnatifida* paste could be produced. The results are shown in Table 3.

TABLE 3

| Class | Type of chelating agent | Particle size (μm) |
| --- | --- | --- |
| Control | — | 300 |
| Test-1 | Sodium citrate | 10 |
| Test-2 | Sodium phosphate | 11 |
| Test-3 | Sodium gluconate | 11 |
| Test-4 | Sodium phytate | 13 |
| Test-5 | Cystein | 18 |
| Test-6 | Methionine | 20 |
| Test-7 | EDTA | 9 |
| Test-8 | HIDS | 9 |

Example 4

Production of *Undaria pinnatifida* Paste 10 kg of *Undaria pinnatifida* (water content: 90%) soaked with water after washing under flowing water was placed in a tank. 0.2 kg of sodium citrate and 5 kg of water were added, and the compositions of these components were respectively subjected to a cutting treatment (treatment using a cutter) using a Stephen cutter for 5 minutes at 10° C. under the atmosphere where the decree of vacuum in the tank was 400 mmHg.

Figure 2:
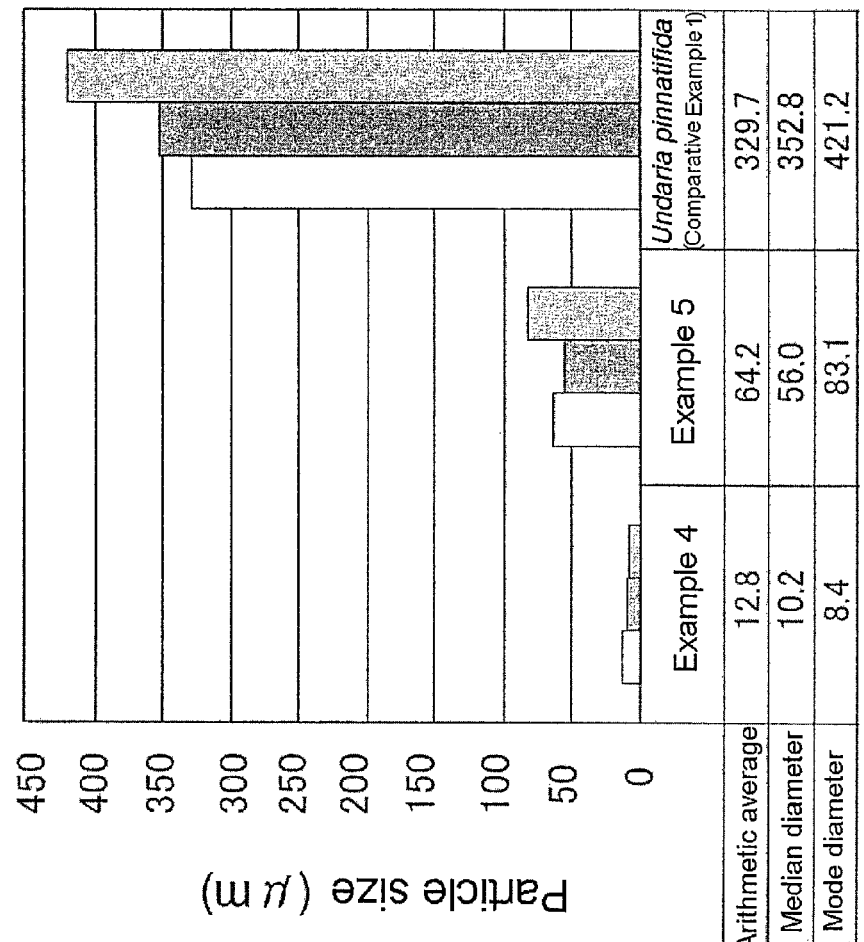
FIG. 2 is a diagram illustrating particle size of the seaweed paste.

Particle size of the resulting *Undaria pinnatifida* paste was measured. An average particle size was 13 μm, and a smooth *Undaria pinnatifida* paste could be obtained. The results are shown in FIGS. 1 and 2.

Comparative Example 1

Commercially available seaweed paste (average particle size: 330 μm) was used.

Next, for the *Undaria pinnatifida* pastes obtained in Example 4 and Comparative Example 1, 20 panelists (12 males and 8 females) performed evaluation by visual observation and sensory evaluation for texture (smoothness in feeling on the tongue) and flavor.

For characteristics noted in visual observation, the seaweed paste prepared in Example 4 did not show large seaweed particles, and it was a homogeneous paste without the feeling of foreign body. In the seaweed paste of Comparative Example 1, significantly large seaweed particles were observed.

The results of sensory evaluation for texture (smoothness in feeling on the tongue) and flavor are shown in Table 4.

TABLE 4

| | Texture (feeling on the tongue) | | | Flavor | | |
| --- | --- | --- | --- | --- | --- | --- |
| | ++ | + | − | ++ | + | − |
| *Undaria pinnatifida* paste of Example 4 | 18 | 2 | 0 | 9 | 8 | 3 |
| *Undaria pinnatifida* paste of Comparative Example 1 | 0 | 6 | 14 | 8 | 10 | 2 |

(Excellent: ++, good: +, poor: −)

As a result, the *Undaria pinnatifida* paste in Example 4 had a texture with very good feeling on the tongue. Many panelists expressed that they hardly felt seaweed particles in comparison with the paste of Comparative Example 1. On the other hand, regarding flavor, the results show that there was no great significance between the pastes of Example 4 and Comparative Example 1.

Example 5

Production of Sea Tangle Paste 10 kg of sea tangle after washed in flowing water and water-dripped (water content: 70%) was placed in a tank. 0.6 kg of sodium citrate and 30 kg of water were added, and the compositions of these components were subjected to a cutting treatment (treatment using a cutter) using a Stephen cutter for 20 minutes at 10° C. under the atmosphere where a degree of vacuum is 400 mmHg.

Particle size of the resulting sea tangle was measured. An average particle size was 64 μm, and smooth sea tangle paste could be obtained.

The results are shown in FIGS. 1 and 2.

Example 6

Production of Japanese Confectionery
A. Materials
  12.4% of egg albumen, 6.2% of egg yolk, 54.3% of white bean jam, 15.5% of white superior soft sugar, 7.0% of wheat flour, 4.6% of the *Undaria pinnatifida* paste obtained in Example 4
B. Production Method
B1. Egg yolk, white bean jam and the *Undaria pinnatifida* paste were mixed.
B2. Meringue was formed with the egg yolk and white superior soft sugar.

B1 and B2 were mixed. Subsequently, the wheat flour was added and the mixture was kneaded. The kneaded material was placed in a mold and steamed, thereby obtaining a Japanese confectionery.

Comparative Example 2

Japanese confectionery was obtained in the same manner as in Example 6 except that commercially available seaweed past (particle size: 330 μm) was used instead of the seaweed paste of the present invention.

20 panelists (12 males and 8 females) made sensory evaluation for quality of the Japanese confectionery. The results are shown in Table 5.

TABLE 5

| | Appearance | Feeling on the tongue | Flavor of seaweed |
| --- | --- | --- | --- |
| Example 6 | ++ | + | ++ |
| Comparative Example 2 | − | − | − |

(Excellent: ++, good: +, poor: −)

The Japanese confectionery of Comparative Example 2 contained rough particles of seaweeds, and the panelists felt feeling of a foreign matter. Furthermore, rough particles resulted in bad feeling on the tongue.

The Japanese confectionery of the present Example had good flavor of seaweed and did not have feeling of foreign matter.

Example 7

Production of Chinese Noodles (Ramen)
A. Materials
  56.3% of hard wheat flour, 14.1% of soft wheat flour, 1.4% of salt, 14.1% of water, 14.1% of the *Undaria pinnatifida* paste obtained in Example 4

B. Production Method

Salt and the *Undaria pinnatifida* paste were added to water, and the mixture was mixed and kneaded with the hard wheat flour and the soft wheat flour. After standing the mixture for a while, the flour was collected and the mixture was kneaded. After standing for over 1 hour, the dough was formed into noodles.

Comparative Example 3

A. Materials 55.5% of hard wheat flour, 13.9% of soft wheat flour, 1.4% of salt, 27.8% of water, 1.4% of brine Normal Chinese noodle (ramen) was formed using the above materials.

Comparative Example 4

Chinese noodle (ramen) was formed in the same manner as in Example 7, except that commercially available seaweed paste (particle size: 330 μm) was used instead of the seaweed paste of Example 4.

In 20 panelists (12 males and 8 females), Example 7 and Comparative Example 3 were compared, and an evaluation was made to determine whether Example 7 has the similar chewiness to Comparative Example 3.

The use of the seaweed paste of Example 4 gave the noodle made without addition of brine a chewiness similar to that of the Chinese noodle (ramen) using normal brine.

In 20 panelists (12 males and 8 females), Example 7 and Comparative Example 4 were compared, and a sensory evaluation for quality was made.

The results are shown in Table 6.

TABLE 6

| | Chewiness | Flavor of seaweed | Appearance | Binding of dough |
|---|---|---|---|---|
| Example 7 | ++ | ++ | + | ++ |
| Comparative Example 4 | − | + | − | − |

(Excellent: ++, good: +, poor: −)

In comparison with Chinese noodle (ramen) using commercially available seaweed paste, Chinese noodle (ramen) containing the seaweed paste of the present invention was found to be excellent in chewiness, flavor of seaweed, appearance, and binding of dough.

The commercially available seaweed paste had rough sizes of particles, which affected the appearance, and also had inferior dispersibility to the seaweed paste of the present invention at the time of formation of dough.

Example 8

Production of Japanese Noodle

A. Materials 32.6% of hard wheat flour, 32.6% of soft wheat flour, 2.2% of salt, 21.7% of tepid water (35° C.), and 10.9% of the *Undaria pinnatifida* paste obtained in Example 4

B. Production Method

Salt and the *Undaria pinnatifida* paste were added to tepid water, the mixture was mixed and kneaded with the hard wheat flour and the soft wheat flour. After standing for a while, the flour was collected and the mixture was kneaded. After standing for over 1 hour, the dough was formed into noodles.

Comparative Example 5

Japanese noodle was formed in the same manner as in Example 8 except that commercially available seaweed paste (particle size: 330 μm) was used instead of the seaweed paste of Example 4.

In 20 panelists (12 males and 8 females), the Japanese noodles of Example 8 and Comparative Example 5 were compared, and an evaluation was made to determine whether Example 8 has the similar chewiness to commercially available product.

The results are shown in Table 7.

TABLE 7

| | Chewiness | Flavor of seaweed | Appearance | Binding of dough |
|---|---|---|---|---|
| Example 8 | ++ | ++ | + | ++ |
| Comparative Example 5 | + | + | − | − |

(Excellent: ++, good: +, poor: −)

In comparison with Japanese noodle blending commercially available seaweed paste, the Japanese noodle containing the seaweed paste of the present invention was found to be excellent in chewiness, flavor of seaweed, appearance, and binding of dough.

The commercially available seaweed paste had rough sizes of particles, which affected on the appearance, and also had inferior dispersibility to the seaweed paste of the present invention at the time of formation of dough.

Example 9

Production of Minced Fish Meat with Seaweeds

10% of the *Undaria pinnatifida* paste obtained in Example 4 was added, and minced fish meat with seaweed was formed.

As a comparative control, minced fish meat with seaweed containing 10% of commercially available seaweed paste added was formed (Comparative Example 6).

Evaluation was made by 10 sensory evaluation panelists. Evaluation items were appearance and texture. The results are shown in Table 8.

TABLE 8

| | Appearance | Texture |
|---|---|---|
| Example 9 | ++ | ++ |
| Comparative Example 6 | − | − |

(Excellent: ++, good: +, poor: −)

In a case of commercially available seaweed paste, particles were rough and feeling of a foreign body was noted. However, the minced fish meat with seaweed using the seaweed paste of the present invention was smooth and was excellent both in appearance and texture of the product.

Furthermore, minced fish meat with seaweed using commercially available seaweed paste is not suitable for swallowing due to its rough particles, but the seaweed paste of the present invention was smooth and suitable for swallowing.

Exemplary Products

A. Materials 10.0% of the seaweed paste obtained in Example 4, 35.0% of fish meat, 4.6% of trehalose, 4.4% of chicken egg, 2.2% of starch, 1.8% of soy sauce, 1.5% of soybean oil, 1.4% of sweetened sake, 0.3% of salt, 38.8% of cold water B. Production Method The fish meat was salt-ground, and seasonings, the Undaria pinnatifida paste of Example 4 and cold water were mixed thereto. The mixture was placed and filled in a mold. After sterilization for 15 minutes at 105° C., the mixture was cooled, quick-frozen (alcohol), and stored frozen.

Example 10

Production of Seaweed Bread

10% of the *Undaria pinnatifida* paste obtained in Example 4 was added, and seaweed bread was formed.

As comparative controls, bread without addition of commercially available seaweed paste (Comparative Example 7) and seaweed bread with 10% of commercially available seaweed paste added (Comparative Example 8) were formed.

Evaluation was made by 10 sensory evaluation panelists. Evaluation items were appearance, moisture retention and using feeling. The results are shown in Table 9.

TABLE 9

|  | Appearance | Texture | Flavor | Taste |
|---|---|---|---|---|
| Comparative Example 7 (0%) | − | − | − | − |
| Comparative Example 10 (10%) | − | + | + | + |
| Example 10 | ++ | ++ | + | + |

(Excellent: ++, good: +, poor: −)

Comparative Example 7 (0%): without addition of commercially available seaweed paste Comparative Example 8 (10%): with addition of 10% of commercially available seaweed paste Example 10 (10%): with addition of 10% of the seaweed paste of the present invention The bread using commercially available seaweed paste had rough particles and had feeling of foreign body.

The bread using the seaweed paste of Example 4 was smooth and had a good appearance. Furthermore, addition of the seaweed paste increased moisture retention and provided texture with elasticity.

A. Materials 48.7% of hard wheat flour, 1.7% of butter, 3.4% of white superior soft sugar, 1.1% of raw flour for confectionery, 1.1% of salt, 0.7% of powder soy sauce, 0.7% of dry yeast, 33.0% of cold water, 9.6% of seaweed paste (the *Undaria pinnatifida* paste obtained in Example 4, sea tangle paste obtained in Example 5)

B. Production Method

The raw materials were kneaded. The dough was stood and fermented for 30-40 minutes at 30-35° C., and was baked for 35-45 minutes at 170-180° C., thereby obtaining bread.

Example 11

Production of Sweet Bean Paste with Seaweeds

5% of the *Undaria pinnatifida* paste obtained in Example 4 was added, and sweat bean paste with *Undaria pinnatifida* was formed.

As comparative controls, sweet bean paste without addition of commercially available seaweed paste (Comparative Example 9) and sweet bean paste with seaweed with 5% of commercially available seaweed paste added (Comparative Example 10) were formed.

Evaluation was made by 10 sensory evaluation panelists. Evaluation items were appearance, texture and quality. The results are shown in Table 10.

TABLE 10

|  | Appearance | Texture | Quality |
|---|---|---|---|
| Comparative Example 9 (0%) | − | − | − |
| Comparative Example 10 (5%) | − | + | − |
| Example 11 | ++ | ++ | ++ |

(Excellent: ++, good: +, poor: −)

Comparative Example 9 (0%): without addition of commercially available seaweed paste Comparative Example 8 (5%): with addition of 5% of commercially available seaweed paste Example 10 (5%): with addition of 5% of the seaweed paste of the present invention The sweet bean paste with seaweed using commercially available seaweed paste had rough particles and had feeling of foreign body.

The sweet bean paste with seaweed using the seaweed paste of the present invention was smooth and had a good appearance, texture and quality.

A. Materials 57.0% of white bean jam, 4.6% of the *Undaria pinaffidia* paste obtained in Example 4, 0.6% of salt, 3.4% of liquid sugar, 5.8% of white superior soft sugar, 28.6% of agar B. Production Method The above raw materials were mixed and stirred while warmed to 80° C. in hot water. The mixture was filled in a case, and heat-sterilized, thereby obtaining sweet bean paste.

Example 12

Production of Seaweed Dressing

20% of the *Undaria pinnatifida* paste obtained in Example 4 was added, and seaweed dressing was formed.

As comparative control, seaweed dressing with 20% of commercially available seaweed paste added (Comparative Example 11) was formed.

Evaluation was made by 10 sensory evaluation panelists. Evaluation items were appearance, flavor, taste, and viscosity. The results are shown in Table 11.

TABLE 11

|  | Appearance | Flavor | Viscosity | Taste |
|---|---|---|---|---|
| Comparative Example 11 | − | − | − | − |
| Example 12 | ++ | + | ++ | + |

(Excellent: ++, good: +, poor: −)

Comparative Example 11 (20%): with addition of 20% of commercially available seaweed paste Example 12 (20%): with addition of 20% of the seaweed paste of the present invention The dressing using commercially available seaweed paste had rough particles and had feeling of foreign body.

The dressing using the seaweed paste of the present invention was smooth and had a good appearance. Furthermore, addition of the seaweed paste provided viscosity and improved adhesiveness to vegetables.

A. Materials

20% of the *Undaria pinnatifida* paste obtained in Example 4, 20% of vinegar, 10% of sugar, 10% of sweetened sake, 6% of salt, 30% of water, 4% of seasoning

Example 13

Seaweed Japanese Paper

5% of the *Undaria pinnatifida* paste obtained in Example 4 was added, and seaweed Japanese paper was formed in accordance with a usual method.

As a comparative control, 5% of commercially available seaweed paste was added, and seaweed Japanese paper was formed in accordance with a usual method (Comparative Example 12). The results are shown in Table 12.

TABLE 12

|  | Appearance | Smoothness | Strength |
|---|---|---|---|
| Comparative Example 12 (5%) | − | − | − |
| Example 13 | ++ | ++ | ++ |

(Excellent: ++, good: +, poor: −)

Comparative Example 12: with addition of commercially available seaweed paste
Example 13: with addition of 5% of the seaweed paste of the present invention The seaweed Japanese paper using commercially available seaweed paste had rough particles and had feeling of foreign body.

The seaweed Japanese paper using the seaweed paste of the present invention was smooth, and could be evenly mixed. Furthermore, the strength of the Japanese paper increased.

Example 14

Production of Seaweed Film

10% of the *Undaria pinnatifida* paste obtained in Example 4 was added, and a seaweed film was formed.

As comparative control, a seaweed film with addition of 10% of commercially available seaweed paste (Comparative Example 13) was formed. The results are shown in Table 13.

TABLE 13

|  | Appearance | Smoothness | Strength |
|---|---|---|---|
| Comparative Example 13 (10%) | − | − | − |
| Example 14 | ++ | ++ | ++ |

(Excellent: ++, good: +, poor: −)

Comparative Example 13 (10%): with addition of 10% of commercially available seaweed paste
Example 14: with addition of 10% of the seaweed paste of the present invention The seaweed film using commercially available seaweed paste had rough particles and had feeling of foreign body.

The seaweed film using the seaweed paste of the present invention was smooth and could be mixed evenly. Furthermore, the film had increased strength.

A. Materials

10% of the *Undaria pinnatifida* paste obtained in Example 4, 5% of starch, 5% of trehalose, 80% of water

Example 15

Production of Seaweed Concrete

1% of the *Undaria pinnatifida* paste obtained in Example 4 was added, and seaweed concrete was formed.

As comparative control, seaweed concrete without addition of commercially available seaweed paste (Comparative Example 14) and concrete with addition of 1% of commercially available seaweed paste (Comparative Example 15) were formed. The results are shown in Table 14.

TABLE 14

|  | Appearance | Strength |
|---|---|---|
| Comparative Example 14 (0%) | − | − |
| Comparative Example 15 (1%) | + | − |
| Example 15 | ++ | ++ |

(Excellent: ++, good: +, poor: −)

Comparative Example 14 (0%): without addition of commercially available seaweed paste
Comparative Example 15 (1%): with addition of 1% of commercially available seaweed paste
Example 15: with addition of 1% of the seaweed paste of the present invention The seaweed concrete using commercially available seaweed paste was difficult to be mixed evenly, and working efficiency was low.

The seaweed concrete using the seaweed paste of the present invention could be mixed evenly, and working efficiency was improved. Furthermore, the concrete had increased strength.

A. Materials 30 kg of cement, 70 kg of sand, 10 kg of water were used for the control concrete, and concrete with addition of 1% of the *Undaria pinnatifida* paste obtained in Example 4 was evaluated.

Example 16

Production of Jelly Drink

A. Steps 2.4 kg of gelatinizing agent was swelled with 3 kg of alcohol, and 250 l of water was added thereto for heating and dissolving (solution A).

250 l of water, 0.5 kg of calcium lactate and 0.3 kg of seaweed paste were mixed (solution B).

Solutions A and B were mixed and gelatinized.

B. Exemplary composition

Gelatinizing agent (gellan) 2.4 parts by weight
Calcium lactate 0.5 parts by weight
Water 500.0 parts by weight
Seaweed paste 0.3 parts by weight
Alcohol 3.0 parts by weight

Comparative Example 16

Using the seaweed paste of the present invention and seaweed paste commercially available from other company, seaweed jelly drinks of the same composition were formed.

20 panelists made sensory evaluation for texture (smoothness in feeling on the tongue) and flavor. The results are shown in Table 15.

TABLE 15

|  | Texture (feeling on the tongue) | | | Flavor | | |
|---|---|---|---|---|---|---|
|  | ++ | + | − | ++ | + | − |
| Example 16 | 12 | 7 | 1 | 6 | 11 | 3 |
| Comparative Example 16 | 0 | 4 | 16 | 3 | 12 | 5 |

(Excellent: ++, good: +, poor: −)

Example 17

Production of Seaweed Facial Washing Cream and Hand Cream

20% of the *Undaria pinnatifida* paste obtained in Example 4, 5% of fish-derived collagen, 0.1% of methylparaben, 0.1% of vitamin C, 0.1% of aromatics, and 74.7% of distilled water were placed in a tank, and were mixed evenly, thereby forming seaweed facial washing cream and hand cream.

As comparative control, seaweed facial washing cream and hand cream were formed in the same manner as in Example 17 except the addition of 20% of commercially available seaweed paste (Comparative Example 17).

Evaluation was made by 10 panelists. Evaluation items were moisture retention, touch and quality of the skin. The results are shown in Table 16.

TABLE 16

| | Moisture retention | Touch | Quality |
| --- | --- | --- | --- |
| Comparative Example 17 (20%) | + | − | + |
| Example 17 | ++ | ++ | ++ |

(Excellent: ++, good: +, poor: −)

Comparative Example 17: with addition of 20% of commercially available seaweed paste Example 17: with addition of 20% of the seaweed paste of the present invention The seaweed facial washing cream and hand cream had rough particles and feeling of foreign body.

The seaweed facial washing cream and hand cream were smooth, and had good moisture retention, texture and quality of the skin.

Example 18

Production of Seaweed Soap

5% of the *Undaria pinnatifida* obtained in Example 4 was added, and a seaweed soap was formed.

As comparative controls, a seaweed soap without addition of commercially available seaweed paste (Comparative Example 18) and a seaweed soap with addition of 5% of commercially available seaweed paste (Comparative Example 19) were formed.

Evaluation was made by 10 panelists. Evaluation items were appearance, moisture retention and using feelings. The results are shown in Table 17.

TABLE 17

| | Appearance | Moisture retention | Quality |
| --- | --- | --- | --- |
| Comparative Example 18 (0%) | − | − | − |
| Comparative Example 19 (5%) | − | + | − |
| Example 18 | ++ | ++ | ++ |

(Excellent: ++, good: +, poor: −)

Comparative Example 18 (0%): without addition of commercially available seaweed paste Comparative Example 19 (5%): with addition of 5% of commercially available seaweed paste Example 18: with addition of 5% of the seaweed paste of the present invention The seaweed soap using commercially available seaweed paste had rough particles and had feeling of foreign body.

The seaweed soap using the seaweed paste of the present invention was smooth and had good appearance, moisture retention and using feelings.

A. Materials 21.8% of distilled water, 9.0% of sodium hydroxide, 64.1% of olive oil, 5.0% of the *Undaria pinnatifida* paste obtained in Example 4, 0.1% of aromatic B. Production Method 1. Sodium hydroxide was mixed with distilled water.
2. Olive oil was heated to about 40° C.
3. The sodium hydroxide water and olive oil prepared above in steps 1 and 2 were mixed until a trace is formed.
4. Seaweed paste and aromatic were mixed.
5. The mixture was placed in a mold and stood.

The results of the present test showed that the *Undaria pinnatifida* paste of the present invention had fine seaweed particles which are hardly felt, and had good texture in comparison with the seaweed paste of other company.

On the other hand, no significant difference was observed in flavor.

While the present invention has been illustrated hereinabove with reference to preferred embodiments of the present invention, the present invention should not be understood as limited to these embodiments. It should be understood that a scope of the present invention is defined only by a scope of claims from the specific description of the preferred embodiments of the invention, it will be apparent to those skilled in the art that the present invention may be implemented within an equivalent scope based on the description and common knowledge of the art. It is also understood that a cited patent, patent application, and reference are incorporated herein by reference in its entirety, as if the contents thereof were specifically described herein.

The invention claimed is:

1. A method of producing seaweed paste comprising the steps of:
    placing seaweed, a chelating agent and water in a tank; and stirring the resulting composition at 0-20° C. to cut the seaweed, wherein the interior of the tank is in a vacuum state, wherein the chelating agent is blended at 0.5-5% by weight with respect to a total amount, wherein a degree of vacuum in the tank is 50 mm Hg to 600 mm Hg, wherein an average particle size of the seaweed in the seaweed paste after cutting the seaweed is 5-100 µm, and wherein the time for cutting treatment of the seaweed is 5-30 minutes.

2. A method of producing seaweed paste according to claim 1, wherein the chelating agent is at least one selected from the group consisting of citric acid, phosphoric acid, gluconic acid, phytic acid, salts of citric acid, phosphoric acid, gluconic acid, and phytic acid, methionine, cystein, EDTA, biodegradable chelating agent and tetrasodium 3-hydroxy-2,2'-iminodisuccinate.

3. A method of producing food comprising the steps of:
    blending the seaweed paste of claims 1 at 1 to 20% by weight with respect to a total amount.

4. A method of producing seaweed paste according to claim 1, wherein water is 5-25 parts by weight and the chelating agent is 0.3-1.0 parts by weight with respect to 10 parts by weight of seaweed.

5. A method of producing seaweed paste according to claim 1, wherein the amount of water added is 0.5-3.0 parts by weight with respect to 1 part by weight of seaweed.

6. A method of producing seaweed paste according to claim 1, wherein the seaweed is selected from the group consisting of *Undaria pinnatifida*, sea tangles and *Nemacystus decipiens*.

7. A method of producing food comprising the steps of:
placing seaweed, a chelating agent and water in a tank; and stirring the resulting composition at 0-20° C. to cut the seaweed, and blending a seaweed paste obtained at 1 to 20% by weight with respect to a total amount of a food, wherein the interior of the tank is in a vacuum state, wherein the chelating agent is blended at 0.5-5% by weight with respect to a total amount, wherein a degree of vacuum in the tank is 50 mm Hg to 600 mm Hg, and wherein an average particle size of the seaweed in the seaweed paste after cutting the seaweed is 5-100 μm, and wherein the time for cutting treatment of the seaweed is 5-30 minutes.

8. A method of producing seaweed paste according to claim 7, wherein the seaweed is selected from the group consisting of *Undaria pinnatifida,* sea tangles and *Nemacystus decipiens.*

* * * * *